(12) United States Patent
Rebinsky et al.

(10) Patent No.: US 9,097,661 B2
(45) Date of Patent: Aug. 4, 2015

(54) ELECTROCHEMICAL SULFUR SENSOR AND THE METHOD OF MAKING THE SAME

(75) Inventors: Douglas A. Rebinsky, Peoria, IL (US); Xiaodong Liu, Peoria, IL (US); Svetlana M. Zemskova, Edelstein, IL (US)

(73) Assignee: Caterpillar, Inc., Peoria, IL (US)

( * ) Notice: Subject to any disclaimer, the term of this patent is extended or adjusted under 35 U.S.C. 154(b) by 300 days.

(21) Appl. No.: 13/015,144

(22) Filed: Jan. 27, 2011

(65) Prior Publication Data

US 2012/0193230 A1  Aug. 2, 2012

(51) Int. Cl.
G01N 27/30    (2006.01)
G01N 27/416   (2006.01)
G01N 33/28    (2006.01)

(52) U.S. Cl.
CPC .......... *G01N 27/4166* (2013.01); *G01N 33/287* (2013.01)

(58) Field of Classification Search
CPC ......................... G01N 27/4166; G01N 33/287
USPC ....................... 204/400–435; 205/775–794.5; 73/53.01–64.56
See application file for complete search history.

(56) References Cited

U.S. PATENT DOCUMENTS

| | | |
|---|---|---|
| 3,853,474 A | 12/1974 | Austin |
| 4,406,754 A | 9/1983 | Narita et al. |
| 4,409,336 A | 10/1983 | Oita |
| 4,431,508 A * | 2/1984 | Brown et al. ................ 204/418 |
| 5,102,528 A * | 4/1992 | Robert ........................ 204/419 |
| 5,342,490 A | 8/1994 | Lever et al. |
| 6,315,886 B1 * | 11/2001 | Zappi et al. ................. 205/701 |
| 6,484,046 B1 | 11/2002 | Say et al. |
| 6,623,620 B2 | 9/2003 | Lai et al. |
| 6,638,415 B1 | 10/2003 | Hodges et al. |
| 6,682,700 B1 | 1/2004 | Mills et al. |
| 6,716,336 B2 * | 4/2004 | Hurland et al. ............ 205/786.5 |
| 6,749,754 B1 | 6/2004 | Holder et al. |
| 7,520,163 B2 | 4/2009 | Kinkade, Jr. et al. |
| 2003/0217922 A1 | 11/2003 | Suganuma et al. |
| 2005/0252790 A1 * | 11/2005 | Dobson et al. .............. 205/789 |
| 2007/0227910 A1 | 10/2007 | Sommer et al. |
| 2008/0006531 A1 | 1/2008 | Holt |
| 2008/0035493 A1 | 2/2008 | Sommer et al. |
| 2008/0165361 A1 | 7/2008 | Kauffman |
| 2008/0257785 A1 | 10/2008 | Varma et al. |
| 2009/0032401 A1 * | 2/2009 | Ronaghi et al. ............. 204/549 |
| 2010/0059375 A1 * | 3/2010 | Weiller et al. .............. 204/433 |

FOREIGN PATENT DOCUMENTS

| | | | |
|---|---|---|---|
| EP | 1935331 A2 * | 6/2008 | |
| EP | 2278322 | 1/2011 | |

* cited by examiner

Primary Examiner — Keith Hendricks
Assistant Examiner — Kourtney S Carlson

(57) ABSTRACT

This disclosure relates to sulfur sensors that utilize sensing materials that can be used to detect a wide range of concentrations including ultra low concentrations of sulfur in liquids, such as below even 15 ppm. The sulfur sensors comprise a sensing electrode having a material that contributes an electronic output to the analysis and a material that contributes an ionic output to the analysis.

20 Claims, 5 Drawing Sheets

US 9,097,661 B2

ELECTROCHEMICAL SULFUR SENSOR AND THE METHOD OF MAKING THE SAME

TECHNICAL FIELD

The present invention relates generally to sensors for detection of sulfur organic compounds. More particularly, the present invention relates to sulfur sensors that utilize sensing materials that can be used to detect a wide range of concentrations including ultra low concentrations of sulfur compounds in liquids, such as below even 15 ppm.

BACKGROUND

It is important to be able to accurately and reliably measure the concentration of sulfur compounds in liquids, as various chemical reactions may take place that would release sulfur compounds into the atmosphere or onto physical structures around the sulfur-containing liquid. For example, the combustion of diesel fuel typically generates sulfur oxides ($SO_2$, $SO_3$) and sulfuric acid (condensate $H_2SO_4$), both of which are components of acid rain. Further, these sulfur compounds have been linked to catalyst deactivation in various aftertreatment components such as diesel particulate filters (DPFs), diesel oxidation catalysts (DOC), NOx trap catalysts, and SCR catalysts. Moreover, sulfuric acid condensation has been linked to severe corrosion of engine components, such as the cooler and piston ring liner components. Such phenomena are found when using both high sulfur (>350 ppm) and low sulfur (15-350 ppm) fuels.

For various reasons, including the sensitivity of aftertreatment components to sulfur compounds, many modern diesel engines are now being designed to use Ultra Low Sulfur Diesel (ULSD) fuel (<15 ppm S). Accordingly, the sulfur level of the fuel source is of utmost importance for optimum machine performance. Examples of known means of detecting sulfur in a wide range of concentrations include ultra-low levels include Flame Photometry Detection (FPD), Inductively Coupled Plasma (ICP) devices, and Monochromatic Wavelength Dispersive X-Ray Fluorescence (WDXRF) spectroscopy, but these methods are more appropriate in the laboratory setting because of the size of the necessary instruments, the duration of test cycles, frequent instrument calibration, and high voltage power requirements. So while sulfur detection in liquids for a wide range of concentrations as well as at levels below 15 ppm is attainable in a laboratory setting, such detection is not feasible in the field or on-board with an accurate, portable, reliable, quick, and inexpensive sensor.

Sulfur organic compounds in diesel fuel can be represented by the formulas R—S—H and R—S—R, where R includes various aliphatic derivatives (saturated or unsaturated), cyclic derivatives, and aromatic derivatives. It is known to those skilled in the art that high sulfur fuels contain predominantly aliphatic and cyclic derivatives, while ultra low sulfur fuels contain mostly aromatic derivatives. Therefore, a sensor operates in wide range of concentrations and should be capable to respond accurately to a variety of sulfur organic species in the liquid.

U.S. Pat. No. 6,716,336 B2 describes an electrochemical sulfur sensor based on an ion conductive ceramic, the sensor being composed of a working (sensing) electrode (porous gold layer) in contact with a liquid (such as fuel), a reference electrode (Ag layer) insulated from the liquid, a reference material (AgS) associated with the reference electrode, and a membrane positioned between the two electrodes. The membrane is in contact with and impermeable to the liquid while it is permeable to an ion that forms a chemical compound with the sulfur species in the liquid. An example is the ion Ag(+); therefore Ag-$\beta$-$Al_2O_3$ was utilized as an Ag-ion conducting ceramic solid electrolyte membrane in the sensor design. Such a sensor exhibits a change in electrical signal (measured as potential) because of the change in ionic conductivity of ceramic membrane materials in contact with sulfur organics in the liquid. Although such a sensor performs well with the "simulated diesel fuel" composed of mostly aliphatic sulfur organics and thiophene, the sensor disclosed in '336 is not successful when it is used with commercially available diesel fuel. Accordingly, a desire for a fast and inexpensive detection of sulfur level in diesel fuels, or possibly an on-board diagnostic tool for determining the same, persists.

SUMMARY OF THE INVENTION

In one aspect, the present disclosure is directed to an electrochemical sulfur sensor for determining a sulfur concentration in a liquid. The electrochemical sulfur sensor comprises a reference electrode and a sensing material including an electronic conductive material and a metal cation. Further, the sensing material is in association with a sensing electrode. Moreover, the sensing material exhibits both electronic and ionic conductivity in the presence of the sulfur-comprising liquid.

In another aspect, the present disclosure is directed to various methods of making the electrochemical sulfur sensor of the present disclosure.

BRIEF DESCRIPTION OF THE DRAWINGS

Whenever possible, the same reference numbers will be used throughout the drawings to refer to the same or like parts.

DETAILED DESCRIPTION

Figure 1:
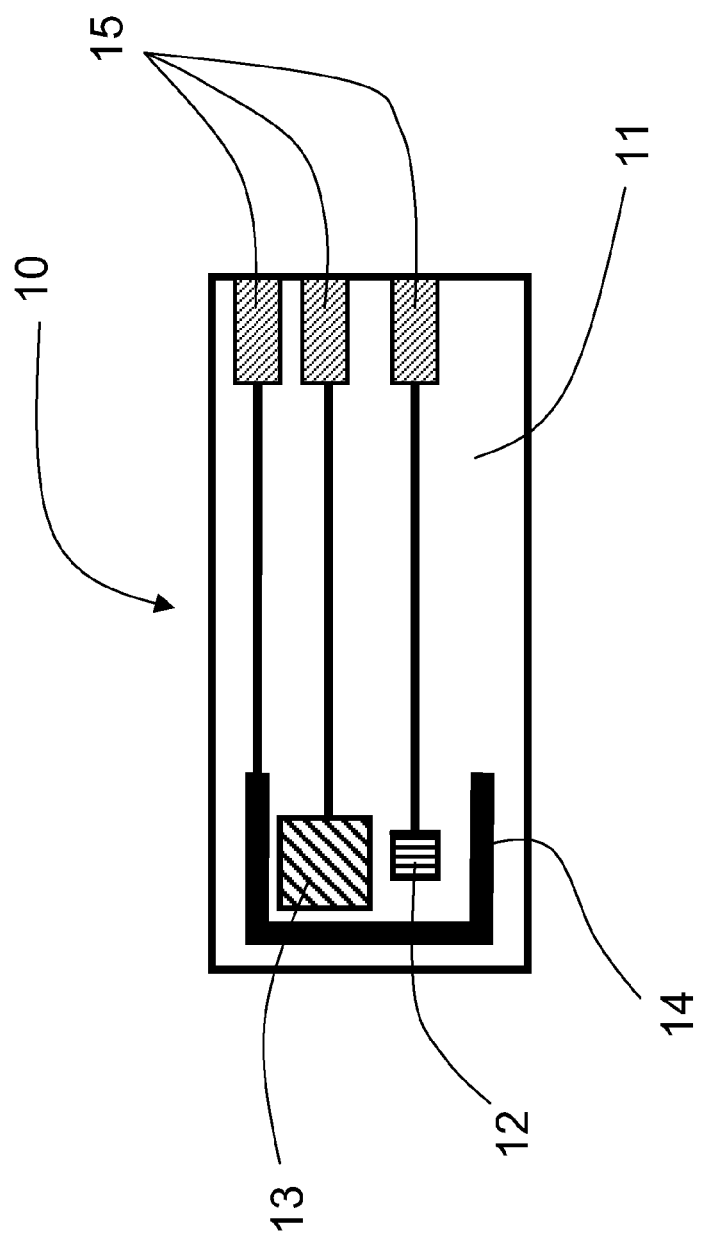
FIG. 1 is a schematic representation of one embodiment of an electrochemical sulfur sensor of the present disclosure.

FIG. 1 illustrates one embodiment of an electrochemical sulfur sensor 10 that comprises three electrodes: a sensing electrode 13, a reference electrode 12, a counter electrode 14, and contacts 15 allowing connection to an electrical measurement device. These three electrodes are associated with an insulating substrate 11, and may be applied thereto using any suitable technique, such as screen-printing. The sensing electrode 13 comprises a sensing material specifically chosen based on the material's ability to exhibiting both ionic and electronic conductivity. It should be understood that electronic herein relates to the activity of electrons or an electron. By doing so, the sensing material of sensing electrode 13 changes its electrical output (current, potential, or resistivity) based on both electronic and ionic factors, yielding a more accurate, robust measurement of the concentration of wide variety of sulfur compounds in the liquid to which the sulfur sensor is exposed. An example of electronic factors contributing to the overall change in conductivity, resistivity, or potential of sensing electrode 13 may include the dipole-dipole interactions between aromatic π-systems of sulfur compounds with labile electronic components of the composite sensing material. An example of ionic factors may include the ion-dipole interactions between metal ions of the composite material and electron pairs from sulfur atoms of sulfur compounds in liquid.

The sensing material of sensing electrode 13 can be in any suitable shape or form, such as bulk tape of suitable material (e.g., lead tape), thick film, fiber and fiber mat, or wire. In one exemplary embodiment, the electronic component of sensing material is a metallic foam, which advantageously increases the total surface area in contact with the liquid. For example, the foam may be a conductive graphite foam. Various conductive materials may be used for fabrication of the composite sensing material such as alloys, conductive carbon, graphite, or other conductive polymers having π-aromatic nature similar to graphite (polythiophene, polypyrrole, etc.). In another exemplary embodiment, the conducting material is in powder form, such as conductive graphite powder or carbon powder in a dried slurry, paste, or sol-gel.

The ionic component of the sensing composite material is introduced by wet impregnation (incipient wetness) of electronic conductive material with metal cations, such as, e.g., $Fe^{2+}$, $Cu^{2+}$, $Ag^{+}$, $Au^{3+}$, $Ni^{2+}$, $Zn^{2+}$, $Pb^{2+}$, $Mo^{4+}$ cations, or mixtures thereof. Electrochemical testing has shown that materials with $Fe^{2+}$, $Cu^{2+}$, $Ag^{+}$, $Zn^{2+}$ and $Ni^{2+}$ are most sensitive to sulfur organic compounds in diesel fuel.

To form the electrochemical sulfur sensor 10 according to the disclosure, a compound comprising a metal cation is dissolved in an aqueous solution. Using iron as an exemplary metal cation, a sufficient amount of Fe-compound, such as $FeSO_4$, is dissolved in water in approximate weight ratios of between about 1:30 and about 1:50. In one example, between about 0.5 g and about 0.6 g, such as about 0.55 g, of $FeSO_4$ may be dissolved in between about 18-22 mL, such as about 20 mL, of $H_2O$. After that, the Fe-aqueous solution is mixed with a solution of AminoPropylThriethylSiloxane (APTS) in EtOH in approximately 1:4 volume ratio, such as between about 1:5 and about 1:3 by volume. Alternatively, other water soluble Fe compounds, aminosiloxanes, or alcohols may be used, as known by those skilled in the art.

Next, a powdered electronic conductive material is added to the metal cation-containing solution in a weight ratio of between about 3:1 to about 4:1 of powdered electronic conductive material to water-soluble Fe compound. In some embodiments, the electronic conductive component of the composite sensing material is a foam or fiber mat type material, in which the metal cation-containing solution may be added to the electronic conductive material. In one example, the powdered electronic conductive material is graphite powder, which is added to a solution of $FeSO_4$, $H_2O$, APTS, and EtOH. In this example, the resulting slurry is allowed to age, such as for at least about 24 hrs or at least about 36 hrs, after which the composite sensing material is filtered out and dried in air. The material may then be washed and cured in a $H_2O$:EtOH with an about 1:1 mixture for at least about 10 hrs and dried.

In another embodiment, a composite sensing material is used to fabricate a solution having a Cu compound. The Cu-comprising solution may include, for example, between about 0.4 g and about 0.5 g, such as about 0.465 g, of $Cu(NO_3)_2$, which is mixed with $H_2O$ in approximate weight ratio of between about 1:40 and about 1:50. The Cu-comprising aqueous solution is then mixed with a solution of APTS and EtOH that has a volume ratio of between about 1:3 and about 1:5, such as about 2 mL APTS and 8 mL EtOH. The Cu-comprising solution is then mixed with the graphite powder and dried for a time sufficient to facilitate drying, such as for at least about 12 hrs or at least about 24 hrs. Afterwards, the material may be washed and cured in $H_2O$:EtOH with an about 1:1 mixture for at least about 30 minutes, such as at least about 1 hr, and dried.

In another embodiment, the composite material slurry is used to fabricate a sensing electrode in the form of a thick film by well-known screen-printed method.

Figure 2:
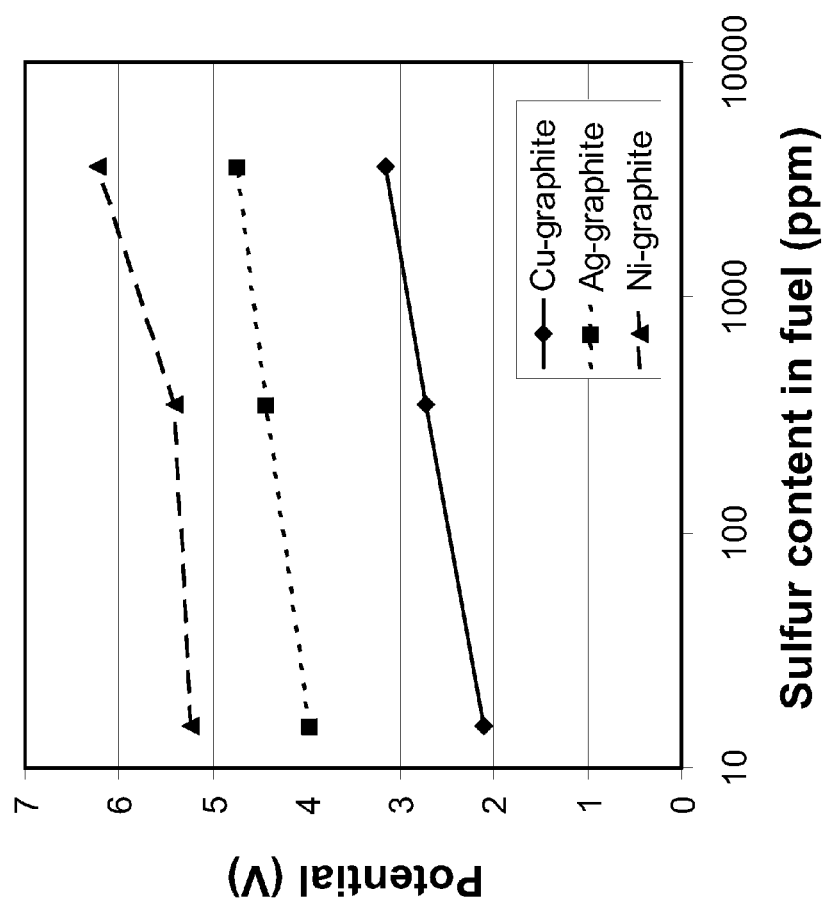
FIG. 2 is a graph showing the change in electrochemical potential of sulfur sensors composed of Ni-graphite, Cu-graphite, and Ag-graphite sensing material during exposure to varying levels of sulfur in the diesel fuel.

FIG. 2 shows the performance of sensors fabricated by screen-printing on insulating substrates and utilizing various composite sensing materials that contain graphite powder impregnated with Ni-, Cu- and Ag-ions. That is, each plot of FIG. 2 shows three different electrochemical sulfur sensors having sensing pads comprising Ni-graphite, Cu-graphite, and Ag-graphite materials. FIG. 2 shows the open circuit potential (OCP) for the electrochemical sulfur sensors as they were exposed to diesel fuels having various sulfur concentrations in a wide range, specifically, about 15 ppm, about 350 ppm, and about 3600 ppm.

Figure 3:
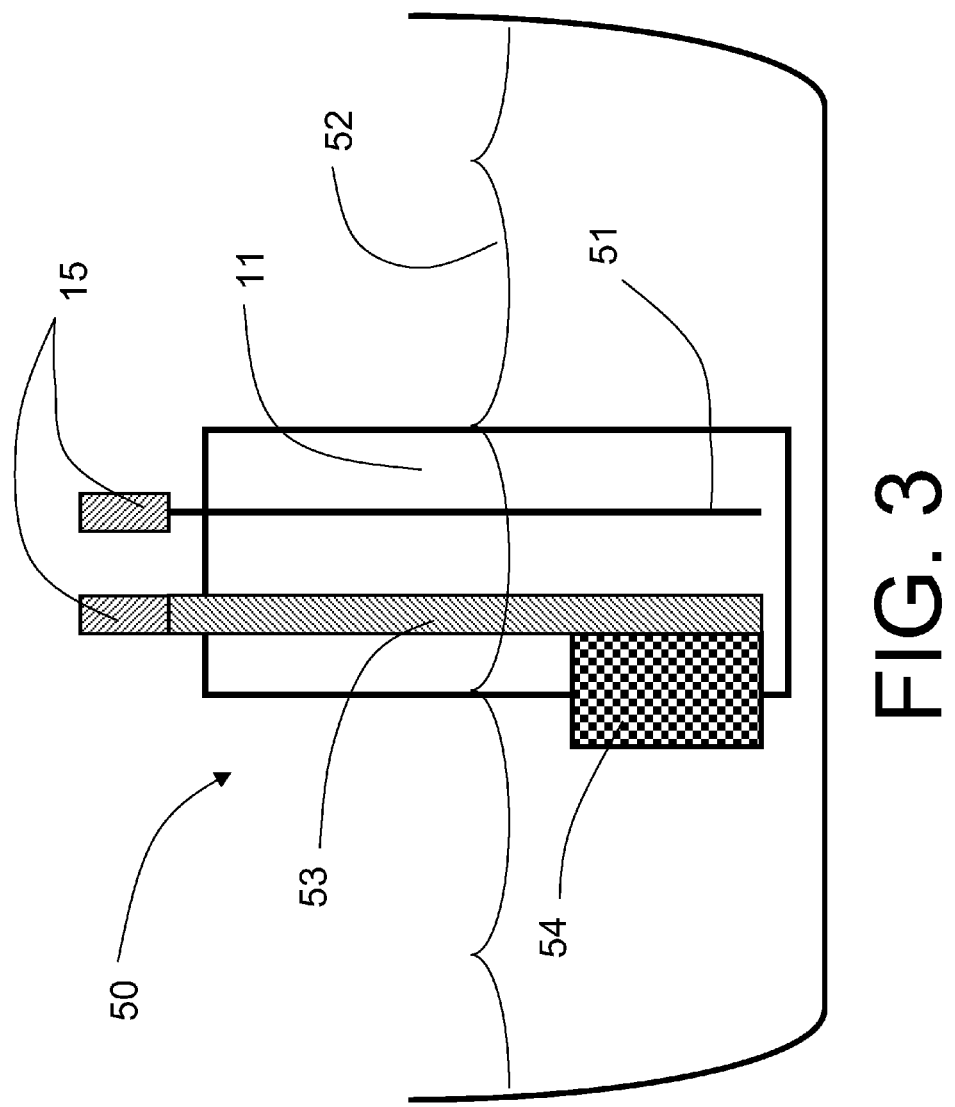
FIG. 3 is a schematic representation of a two-electrode electrochemical sulfur sensor.

FIG. 3 shows another embodiment of the disclosure, which is a two-electrode design of the electrochemical sulfur sensor, indicated as 50. Two-electrode electrochemical sulfur sensor 50 includes a sensing electrode pad 54 made of Cu-graphite composite material and utilizes a conductive metal tape, such as, Cu tape, affixed to a sensing electrode 53, where the conductive metal tape functions as a contact lead and a mechanical support for sensing electrode pad 54. Two-electrode electrochemical sulfur sensor 50 further includes a reference electrode 51, such as an Ag-based wire. An insulating material (not shown), such as a PTFE insulating layer, may be used to electrically shield reference electrode 51 for improved stability of its potential.

To form two-electrode electrochemical sulfur sensor 50, a sol-gel composite is formed comprising a metal cation component and an electronic component, such as graphite. The sol-gel composite is then applied to the conductive metal tape and cured for a sufficient time, such as at least about 12 hrs, at least about 24 hrs, or at least about 36 hrs.

Figure 4:
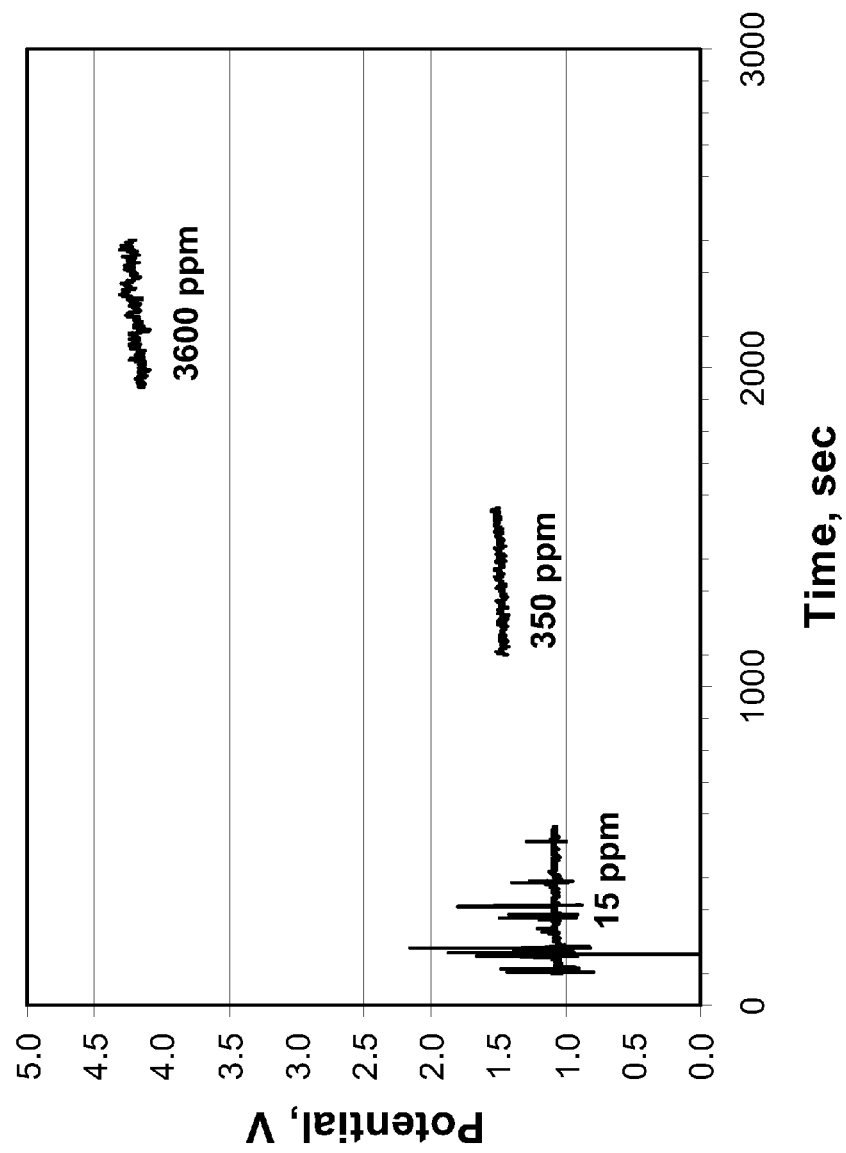
FIG. 4 is a graph showing the electrochemical potential of a sulfur sensor wherein the sulfur sensor comprises Fe-graphite composite material forming a sensing electrode.
Figure 5:
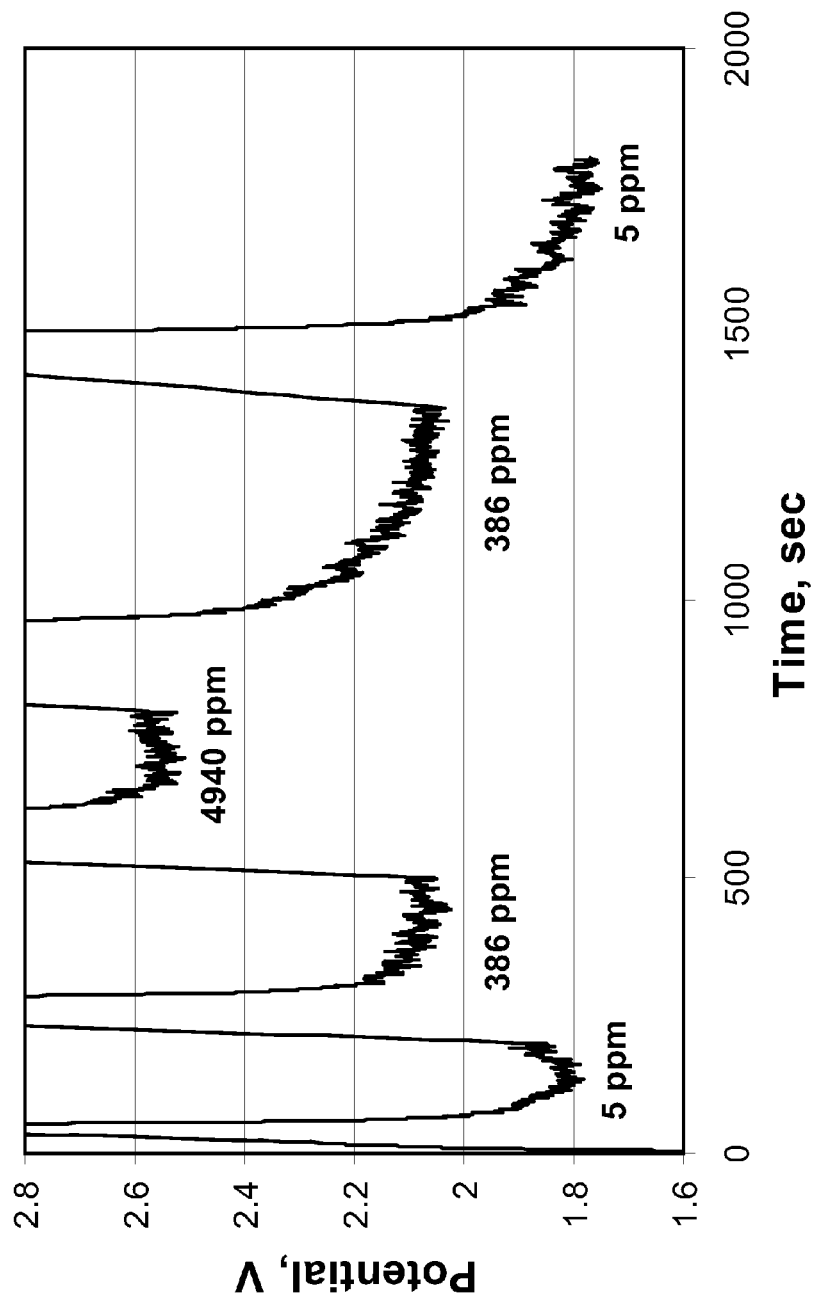
FIG. 5 is a graph showing the electrochemical potential of a sulfur sensor wherein the sulfur sensor comprises composite Cu-graphite forming a sensing electrode.

The ability of two-electrode electrochemical sulfur sensor 50 to be repeatedly used in various fuels is shown by further data in FIGS. 4 and 5. In FIG. 4, the electrochemical potential or OCP was measured for a two-electrode electrochemical sulfur sensor 50 having composite Fe-graphite sensing pads as it was immersed in diesel fuels having about 15 ppm, about 350 ppm, and about 3600 ppm sulfur. In FIG. 5, the electrochemical potential or OCP was measured for a two-electrode electrochemical sulfur sensor 50 having composite Cu-graphite sensing pads as it was immersed in diesel fuels 52 having about 5 ppm, about 386 ppm, and about 4940 ppm sulfur. The sensors were rinsed with octane between exposures to each diesel fuel sample.

Industrial Applicability

Once an electrochemical sulfur sensor is assembled according to this disclosure, the sensor is exposed to a liquid, such as a fuel. After a response time, such as, at least about 1000 sec, at least about 2000 sec, at least about 3000 sec, at least about 4000 sec, or at least about 5000 sec, the sensor undergoes a change in potential of sensing electrode relative to the reference electrode. This change in potential, which is based on both electronic and ionic factors, can then be correlated to a sulfur concentration in the liquid.

The electrochemical sulfur sensor may be used for detection of sulfur organic compounds in diesel fuel as it is being introduced into a vehicle, at a fueling location before the fuel is introduced into the vehicle, or after the fuel is in the vehicle while diagnosing a vehicle in its environment. The electrochemical sulfur sensor may also be used for continuous in-line monitoring of the sulfur organic compounds in the fuel during a fossil fuel desulfurization process. The electrochemical sulfur sensor can also be used as a part of a portable field fuel test kit. Standard electrochemical cells and other commercial equipment may be used to measure the electrochemical sulfur sensor output potential in various fuel samples.

Utilization of improper fuels may result in malfunctioning or premature failure of various aftertreatment components, or both. Therefore, in another application, an on-board sensor can be used for measuring the amount of sulfur compounds in the fuel and determining whether the measured concentration is out of compliance with a predetermined range. The method further includes providing a signal when the measured concentration is out of compliance with such predetermined range.

In another aspect, the disclosure relates to a method for determining whether a product warranty applies to cover the cost of replacing a failed component of an aftertreatment system. The method includes measuring a concentration of sulfur compounds in the fuel and determining whether the measured concentration is out of compliance with a predetermined range. The method further includes providing an out-of-compliance warning signal when concentration of sulfur compounds in fuel is out of compliance with the predetermined range and determining a usage value representative of a usage of the system while the measured fuel property is out of compliance with the predetermined range.

In yet another aspect, the disclosure relates to a diagnostic system capable of monitoring the concentration of sulfur compounds in fuel. The system includes a sensor for determining sulfur concentration in fuel and a controller in communication with the sensor. The controller is configured to receive the sulfur sensor output signal, to determine whether the sulfur concentration in fuel is out of compliance with a predetermined range, and to provide a warning signal when sulfur concentration is out of compliance with the predetermined range. In addition, the controller is configured to communicate with an on-board computer to create an "out of compliance" record, which can be used to determine if the warranty cost applied for a failed aftertreatment component.

Although the present inventions have been described with reference to exemplary embodiments, workers skilled in the art will recognize that changes may be made in form and detail without departing from the sprit and scope of the invention. For example, although different exemplary embodiments may have been described as including one or more features providing one or more benefits, it is contemplated that the described features may be interchanged with one another or alternatively be combined with one another in the described exemplary embodiments or in other alternative embodiments. Because the technology of the present invention is relatively complex, not all changes in the technology are foreseeable. The present invention described with reference to the exemplary embodiments and set forth in the flowing claims is manifestly intended to be as broad as possible. For example, unless specifically otherwise noted, the claims reciting a single particular element also encompass a plurality of such particular elements.

What is claimed is:

1. An electrochemical sulfur sensor for determining a concentration of sulfur compounds in a liquid, the electrochemical sulfur sensor comprising:
   a reference electrode; and
   a sensing electrode including a sensing material including an electronic conductive material wet impregnated with a metal cation, wherein the wet impregnation of the electronic conductive material includes dissolving the metal cation in water and adding the electronic conductive material to the resulting aqueous solution prior to formation of the sensing electrode;
   wherein the sensing material exhibits both electronic and ionic conductivity in the presence of the liquid.

2. The electrochemical sulfur sensor of claim 1 wherein the form of the electronic conductive material is selected from the group consisting of graphite foam, metal coupons, tape, fiber, fiber mesh, powder, sintered powder, and thick and thin film depositions.

3. The electrochemical sulfur sensor of claim 1 wherein the electronic conductive material is a graphite foam.

4. The electrochemical sulfur sensor of claim 1 wherein the metal cation is selected from the group consisting of $Fe^{2+}$, $Cu^{2+}$, $Ag^+$, $Au^{3+}$, $Ni^{2+}$, $Zn^{2+}$, $Pb^{2+}$, $Mo^{4+}$ and combinations thereof.

5. The electrochemical sulfur sensor of claim 1 wherein the reference electrode is a wire comprising Ag, Au, Pt, and combinations thereof.

6. The electrochemical sulfur sensor of claim 1 wherein the electronic conductive material is affixed to a copper-based metal tape.

7. The electrochemical sulfur sensor of claim 6 further including an insulating layer between the reference electrode and the sensing electrode affixed to a copper-based metal tape.

8. The electrochemical sulfur sensor of claim 7 wherein the insulating layer includes PTFE.

9. The electrochemical sulfur sensor of claim 1 wherein the sensing electrode includes a metal composite matrix with graphite, wherein graphite particles are dispersed with metal particles in the metal composite matrix.

10. An electrochemical sulfur sensor for determining a concentration of sulfur compounds in a liquid, comprising;
    a reference electrode;
    a sensing electrode including a composite material of graphite wet impregnated with a metal cation, wherein the wet impregnation of the graphite includes dissolving the metal cation in water and adding the graphite in powdered form to the resulting aqueous solution prior to formation of the sensing electrode; and
    an insulating layer between the reference electrode and the sensing electrode.

11. The sensor of claim 10, wherein the metal cation is selected from the group consisting of $Fe^{2+}$, $Cu^{2+}$, $Ag^+$, $Au^{3+}$, $Ni^{2+}$, $Zn^{2+}$, $Pb^{2+}$, $Mo^{4+}$, and combinations thereof.

12. A method for forming an electrochemical sulfur sensor for determining a sulfur concentration in a liquid, the electrochemical sulfur sensor including a reference electrode and a sensing material including an electronic conductive material and a metal cation, wherein the sensing material is in association with a sensing electrode, the method comprising:
    forming the sensing material by wet impregnating the electronic conductive material with the metal cation, wherein the wet impregnating includes dissolving the metal cation in water and adding the electronic conductive material to the resulting aqueous solution prior to formation of the sensing electrode.

13. The method of claim 12 wherein the metal cation is $Fe^{2+}$.

14. The method of claim 12 wherein the conductive material is in powder form.

15. The method of claim 14 wherein the powder is a graphite powder.

16. The method of claim 14, further including;
   combining the aqueous solution with the powdered conductive material to form a composite slurry;
   aging the composite slurry for at least about 24 hours;
   curing the aged slurry for at least about 10 hours; and
   drying the cured slurry.

17. The method of claim 12 wherein the conductive material is a foamed material.

18. The method of claim 17 wherein the foamed material is graphite foam.

19. The method of claim 17, further including;
   combining the aqueous solution with the graphite foamed material;
   aging the combined solution and foamed material for at least about 12 hours;
   curing the aged foamed material for at least about 30 minutes; and
   drying the cured slurry.

20. The method of claim 12 wherein the solution is a sol-gel solution; the method further including:
   combining the sol-gel solution with a graphite foam;
   applying the combined sol-gel solution and graphite foam to a conductive metal tape.

* * * * *